United States Patent [19]
Hongo et al.

[11] Patent Number: 5,773,585
[45] Date of Patent: Jun. 30, 1998

[54] GLUTAMATE DEHYDROGENASE FROM PSEUDOMONAS

[75] Inventors: Noriyuki Hongo; Shizuo Hattori; Kazumi Yamamoto; Shinichi Teshima; Yoshihisa Kawamura, all of Tsuruga, Japan

[73] Assignee: Toyo Boseki Kabushiki Kaisha, Osaka, Japan

[21] Appl. No.: 667,357

[22] Filed: Jun. 21, 1996

Related U.S. Application Data

[63] Continuation of Ser. No. 386,768, Feb. 10, 1995, abandoned.

[30] Foreign Application Priority Data

Feb. 16, 1994 [JP] Japan .................................. 6-019448
Jun. 6, 1994 [JP] Japan .................................. 6-123883

[51] Int. Cl.⁶ .................................................. C12N 9/02
[52] U.S. Cl. .................... 435/189; 435/253.3; 435/874
[58] Field of Search ................................ 435/189, 874, 435/253.3

[56] References Cited

PUBLICATIONS

Chávez et al., An NAD–Specific Glutamate Dehydrogenase from Cyanobacteria, Federation of European Biochemical Societies, 1991, vol. 285, No. 1, pp. 35–38.

Winnacker et al., Purification and Properties of a NAD–Dependent Glutamate Dehydrogenase from Clostridium $SB_4$, Biochimica et Biophysica Acta, 1970, vol. 212, pp. 225–242.

Johnson et al., Purification and Characterization of Glutamic Acid Dehydrogenase and α–Ketoglutaric Acid Reductase from *Peptococcus aerogenes*, Canadian J. Microbiol., 1972, vol. 18, pp. 881–892.

Tokushige et al., J. Biochem., 85, 1415–20, 1979.

Früh et al., Arch. Microbiol., 1985, 141, 170–76.

Joannou et al., FEMS Microbiology letters, 90, 1992, 205–210.

Mulligan et al., App. & Envir. Microbiol., 1989, 55(11), 3016–19.

Bellion, Proceedings of the $4^{th}$ Int'l. Symposium on Microbiol growth on 1 carbon Compounds, 1984, 170–173.

*Primary Examiner*—Irene Marx
*Attorney, Agent, or Firm*—Foley & Lardner

[57] ABSTRACT

A novel glutamate dehydrogenase is derived from the genus Pseudomonas and is specific to L-glutamic acid, requires $NAD^+$ and NADH as coenzymes, does not act on $NADP^+$ and NADPH, has an optimum pH 10.5–11.5 (oxidative deamination), a pH stability of 5–10 (at 25° C.; 20 hours), an optimum temperature of about 60° C. (oxidative deamination) and a molecular weight of about 280,000 (gel filtration) or about 41,000 (SDS-PAGE) and is not activated by ADP.

5 Claims, 10 Drawing Sheets

GLUTAMATE DEHYDROGENASE FROM PSEUDOMONAS

This application is a continuation of application Ser. No. 08/386,768, filed Feb. 10, 1995 now abandoned.

The present invention relates to a novel glutamate dehydrogenase and, more particularly, it relates to a glutamate dehydrogenase which is thermally stable and also stable in a reagent solution and is suitable for measuring the amounts of glutamic acid and ammonia in a reagent solution and also to a reagent composition for measuring ammonia using said enzyme.

Glutamate dehydrogenase is widely available in animals, plants, microorganisms, etc. and is classified into three groups depending upon its coenzyme specificity. An enzyme (EC1.4.1.2) which requires $NAD^+$ as a coenzyme is present in higher plants, bacteria, fungi and yeasts and participates in a decomposition of glutamic acid. Another enzyme (EC1.4.1.3) which requires $NAD^+$ and $NADP^+$ as coenzymes is present in animals, bacteria and fungi and that derived from bovine liver is most well-known. Still another enzyme (EC1.4.1.4) which requires $NADP^+$ as a coenzyme is present in bacteria, yeasts and fungi and participates in a biosynthesis of glutamic acid.

Glutamate dehydrogenase can be used for measuring the amounts of glutamic acid and ammonia utilizing its oxidative deamination and reductive amination. In addition, it can be used for measuring the amounts of urea nitrogen, creatinine, leucine aminopeptidase and glutamic-oxaloacetic transaminase together with various enzymes.

With respect to a glutamate dehydrogenase which has been used widely, that which is derived from bovine liver may be listed. Said enzyme is an enzyme (EC1.4.1.3) which is capable of using $NAD^+$ and $NADP^+$ and requires ADP as an activator and is known to exhibit little stability. Enzymes of the genus Proteus and those derived from yeasts are commercially available too. They are $NADP^+$-dependent glutamate dehydrogenase (EC1.4.1.4) and, since it requires $NADP^+$, there is an advantage that unfavorable side reaction does not take place in a measurement of ammonia, etc. in a biological sample. On the other hand, however, there is a disadvantage that NADPH ($NADP^+$) is expensive as compared with NADH ($NAD^+$).

Moreover, under the recent state where liquid reagents which do not require the labor for their preparation, it has been known that NADPH exhibits a significantly inferior stability in a liquid as compared with NADH.

In view of the above-mentioned background, there has been a demand for developing a glutamate dehydrogenase which is capable of using $NAD^+$ (NADH) as a coenzyme, stable to heat, exhibits a high stability in a reagent solution and does not require ADP for its activation.

On the other hand, measurement of ammonia, especially that in blood, is essential as an index on diagnosis of liver diseases. Further, the amount of urea nitrogen is important in checking the state of protein intake, metabolic function of protein, renal function, etc. and is useful as an index for diagnosis of kidney failure, edema, obstructive uropathy, diabetes, hyperthyroidism, hepatic failure, etc. Moreover, creatinine is very useful for diagnosing uraemia, chronic hepatitis, actute brightism, gigantism, tetanic myodystrophia, etc.

Quantitative determination of ammonia may be classified into an electrode method, a colorimetric method, an enzymatic method (a UV method), etc. Among them, the enzymatic method is a method whereby removal of protein is not required and only ammonia can be quantitatively and specifically determined using a sample of small quantity. The method using a glutamate dehydrogenase (Clin. Chim. Acta, 39, 472(1972)) is a leading method at present.

The reaction of glutamate dehydrogenase requires NADH or NADPH and the amount of ammonia is determined by measuring a decrease in an absorbance of NAD(P)H at 340 nm. Glutamate dehydrogenase may be classified depending upon the source of the enzyme into an NADH-specific enzyme, an NADPH-specific enzyme and an NADH- and NADPH-dependent enzyme.

In the measurement of urea nitrogen and of creatinine, the UV method is preferred because of its precision and low cost. Usually, ammonia is produced by adding urease and a creatinine deiminase in a method of measuring urea nitrogen and creatinine, respectively, followed by linking to a method wherein a glutamate dehydrogenase is used (Rinsho Kagaku, vol.8, no.1, page 93(1979) and Kensa to Rinsho, vol.19, no.1, page 1019(1991)).

With respect to a glutamate dehydrogenase which is used widely at present, an enzyme derived from bovine liver is available and is capable of using both NADH and NADPH. However, said enzyme required ADP as an activator and it has been widely known that, in a reagent for measuring ammonia containing said enzyme, ADP is necessary as an activator as well as a stabilizer.

On the other hand, another glutamate dehydrogenase which does not require ADP is also known and it is prepared from microorganisms of the genus Proteus and yeast. It has been further said that, since said enzyme is specific to NADPH, it is hardly affected by other enzymes in the sample. However, there are disadvantage that NADPH is expensive as compared with NADH and is without good stability upon storage and accordingly that it lacks a storage stability in liquid reagents which have been diffused recently.

The present inventors have carried out extensive studies for solving the problems concerning the conventional glutamate dehydrogenase and found a novel glutamate dehydrogenase from a microorganism belonging to the genus Pseudomonas whereby the present invention has been achieved.

Thus, the present invention relates to a glutamate dehydrogenase having the following physicochemical properties.

(1) It catalyzes the following reaction.

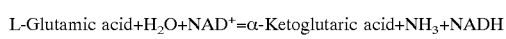

L-Glutamic acid+$H_2O$+$NAD^+$=α-Ketoglutaric acid+$NH_3$+NADH (2) Substrate specificity:

It is specific to L-glutamic acid. It requires $NAD^+$ and NADH as coenzymes and does not act on $NADP^+$ and NADPH.

(3) Thermal stability:

It is stable up to about 60° C. (at pH 8.3 for ten minutes).

(4) It is not activated by ADP.

One of the embodiments of the present invention is a glutamate dehydrogenase having the following physicochemical properties.

(1) It catalyzes the following reaction.

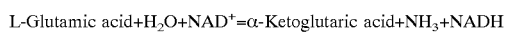

L-Glutamic acid+$H_2O$+$NAD^+$=α-Ketoglutaric acid+$NH_3$+NADH (2) Substrate specificity:

It is specific to L-glutamic acid. It requires $NAD^+$ and NADH as coenzymes and does not act on $NADP^+$ and NADPH.

(3) Thermal stability:
It is stable up to about 60° C. (at pH 8.3 for ten minutes).
(4) It is not activated by ADP.
(5) Specific activity: not less than 300 units/mg
(6) Influence of surfactants: not inhibited by Brils (poloxyethylene long chain alcohol ether)

Another embodiment is a glutamate dehydrogenase having the following physicochemical properties.
(1) It catalyzes the following reaction.

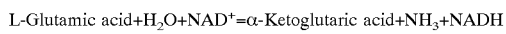

L-Glutamic acid+$H_2O$+$NAD^+$=α-Ketoglutaric acid+$NH_3$+NADH (2) Substrate specificity:
It is specific to L-glutamic acid. It requires $NAD^+$ and NADH as coenzymes and does not act on $NADP^+$ and NADPH.
(3) Optimum pH: 10.5–11.5 (an oxidative deamination)
(4) pH stability: pH 5–10 (at 25° C. for 20 hours)
(5) Optimum temperature: about 60° C. (an oxidative deamination)
(6) Thermal stability: stable up to about 60° C. (at pH 8.3 for ten minutes).
(7) Molecular weight: about 280,000 (by a gel filtration); about 41,000 (by an SDS-PAGE)
(8) It is not activated by ADP.

Still another embodiment is a glutamate dehydrogenase having the following physicochemical properties.
(1) It catalyzes the following reaction.

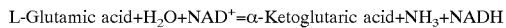

L-Glutamic acid+$H_2O$+$NAD^+$=α-Ketoglutaric acid+$NH_3$+NADH (2) Substrate specificity:
It is specific to L-glutamic acid. It requires $NAD^+$ and NADH as coenzymes and does not act on $NADP^+$ and NADPH.
(3) Optimum pH: 10.5–11.5 (an oxidative deamination)
(4) pH stability: pH 5–10 (at 25° C. for 20 hours)
(5) Optimum temperature: about 60° C. (an oxidative deamination)
(6) Thermal stability: stable up to about 60° C. (at pH 8.3 for ten minutes).
(7) Molecular weight: about 280,000 (by a gel filtration); about 41,000 (by an SDS-PAGE)
(8) It is not activated by ADP.
(9) Specific activity: not less than 300 units/mg
(10) Influence of surfactants: not inhibited by Brijs (poloxyethylene long chain alcohol ether)

Still further embodiment is a glutamate dehydrogenase having the above-mentioned properties which is produced by microorganisms such as that belonging to the genus Pseudomonas or preferably FERM P-14092 which is a microorganism belonging to the genus Pseudomonas.

With respect to the source of the enzyme of the present invention, any of animals, plants, microorganisms, etc. may be used so far as it is capable of producing the glutamate dehydrogenase having the above-mentioned properties. Preferred one is a microorganism belonging to the genus Pseudomonas which is capable of producing a glutamate dehydrogenase having the above-mentioned properties and, more preferably, Pseudomonas sp. 433-3.

Pseudomonas sp. 433-3 used in the present invention is a strain isolated from the soil collected in Sakihagara-cho, Fuhagun, Gifu Prefecture, Japan by the present inventors and its mycological properties are as follows.
(a) Morphological characteristics:
(1) Shape: short rods
(2) Size of a cell: 0.7–1.0×0.3 μm
(3) Pleomorphism of a cell: None
(4) Mobility: Positive having a polar flagelium
(5) Sporulation: None
(b) Growth condition on each medium:
(1) Broth agar plate medium: After 48 hours of culture at 30° C., a yellow to orange colony is formed. The periphery of the colony is labarlobulate and convex. The colony has a rough, ceracous and translucent surface.
(2) Bouillon culture: The strain grows satisfactorily and the bouillon becomes turbid uniformly. Sedimentations are only a few.
(3) Bouillon gelatin culture: The strain grows satisfactorily and only the upper portion thereof becomes filiform. Gelatin is not liquefied.
(4) Litmus milk: Color is not changed. Milk is degradated.
(5) Macconkey agar plae medium: No growth
(6) Phenylethyl alcohol agar plate medium: No growth
(c) Physiological characteristics:

| | | |
|---|---|---|
| (1) Gram staining: | | – (negative) |
| (2) Reduction of nitrate: | | – |
| (3) Denitrification: | | – |
| (4) MR test: | | – |
| (5) VP test: | | – |
| (6) Production of indole: | | – |
| (7) Production of hydrogen sulfide: | | – |
| (8) Hydrolysis of starch: | | + (positive) |
| (9) Degradation of Tween 80: | | – |
| (10) Utilization of citric acid: | | |
| | Koser's medium: | – |
| | Christensen's medium: | – |
| (11) Production of pigment: | | Yellow pigment is produced in a cell. |
| (12) Urease: | | – |
| (13) Oxidase: | | – |
| (14) Catalase: | | + |
| (15) β-Galactosidase | | + |
| (16) Arginine dihydrolase: | | – |
| (17) Lysine carboxylase | | – |
| (18) Ornithine carboxylase | | – |
| (19) Tryptophan deaminase | | – |
| (20) β-Glucosidase | | + |
| (21) Protease | | – |
| (22) Deoxyribonuclease: | | – |
| (23) Growth conditions: | | |
| | Growth temperature | |
| | 20° C. | + |
| | 25° C. | + |
| | 30° C. | + |
| | 37° C. | – |
| | 40° C. | – |
| | 50° C. | – |
| | Growth pH | |
| | pH 3 | – |
| | pH 4 | – |
| | pH 5 | – |
| | pH 6 | + |
| | pH 7 | + |
| | pH 8 | + |
| | pH 9 | + |
| | pH 10 | – |
| (24) Utilization of nitrogen source (Carbon source: D-Glucose): | | |
| | Glutamate | + |
| | Sodium nitrate | + |
| | Ammonium sulfate | + |
| (25) Bahavior toward oxygen: | | Aerobic |
| (26) O-F Test (Hugh Leifson method) | | O (oxidation) |

-continued

(27) Production of acid and gas from sugar:

|  | Acid | Gas |
|---|---|---|
| L-Arabinose | − | − |
| D-Xylose | − | − |
| D-Glucose | + | − |
| D-Mannose | − | − |
| D-Fructose | − | − |
| D-Galactose | − | − |
| Maltose | − | − |
| Sucrose | − | − |
| Lactose | − | − |
| Trehalose | − | − |
| D-Sorbitol | − | − |
| D-Mannitol | − | − |
| Inositol | − | − |
| Glycerol | − | − |
| Starch | − | − |
| Rhamnose | − | − |
| D-Melibiose | − | − |
| D-Amygadlin | − | − |

(28) Utilization of organic compound:

| D-Glucose | + |
|---|---|
| D-Arabinose | + |
| D-Mannose | + |
| D-Mannitol | − |
| N-Acetyl-D-glucosamine | + |
| Maltose | + |
| Potassium gluconate | − |
| N-Caprate | − |
| Adipic acid | − |
| DL-Malic acid | − |
| Sodium citrate | − |
| Phenyl acetate | − |

An experiment for identifying the above-mentioned mycological characteristics was conducted mostly in accordance with "Classification and Identification of Microorganisms" (in Japanese) edited by T. Hasegawa, Revised Edition (1985), Gakkai-Shuppan Senta (Academy Publishing Center).

The classification and identification of the microorganisms are based on "Bergey's Manual of Systematic Bacteriology" (1984) and "International Journal of Systematic Bacteriology", vol.27 (2), pages 133–146 (1977).

Based on the above literatures and mycological properties, the present microorganism has been considered to belong to the genus Pseudomonas. In addition, many characteristic properties of the present microorganism are identical with those of Pseudomonas paucimobilis but neither production of deoxyribonuclease nor degradation of Tween 80 was noted. Therefore, the present microorganism differs from the above and has been named Pseudomonas sp. 433-3 (FERM P-14092).

In the manufacture of the enzyme of the present invention, the microorganism which is capable of producing a glutamate dehydrogenase having the above-mentioned characteristics is cultivated in a culture medium and a glutamate dehydrogenase is collected from the resulting culture.

With respect to a culture medium used for cultivating the microorganism which produces a glutamate dehydrogenase, any of synthetic and natural media may be used so far as it contains suitable amounts of carbon source, nitrogen source, inorganic substances and other nutrients. Examples of the applicable carbon source are glucose and glycerol. Examples of the applicable nitrogen source are nitrogen-containing natural substances such as peptones, meat extract and yeat extract and compounds containing inorganic nitrogen such as ammonium chloride and ammonium citrate. Examples of the applicable inorganic substances are potassium phosphate, sodium phosphate and magnesium sulfate.

It is preferred that sodium glutamate is added to a culture medium as an inducer for a glutamate dehydrogenase.

Usually, a cultivation is carried out by means of a shaking culture or an aeration-agitation culture. The culture temperature is 20°–30° C. or, preferably, 25°–30° C. while the pH of the medium is within a range of 6–9 or, preferably, 7–8. With regard to the culture period, growth is usually noted within 1–3 days whereupon a glutamate dehydrogenase is produced and accumulated in the cells.

In purifying the enzyme of the present invention, any of the common purifying means may be applied. With respect to an extraction method, any of disintegration by means of ultrasonication, mechanical disintegration using glass beads and a French press may be used. The extract may be purified by means of a salting-out method using ammonium sulfate or the like, a coagulating method using polyethyleneimine or the like or an ion exchange chromatographic method using DEAE-Sepharose, CM(carboxymethyl)-Sepharose, etc. Crude enzyme solution or purified one prepared by the above-mentioned method may be pulverized, for example, by a spray-drying or by a freeze-drying.

A method of measuring an activity of the glutamate dehydrogenase of the present invention by means of a reductive amination will be as follows.

The following reaction mixture solution is prepared:

| 0.1M Tris-HCl buffer (pH: 8.3) | 25 ml |
|---|---|
| 3.3M $NH_4Cl$ solution | 2 ml |
| 0.225M α-Ketoglutaric acid solution | 1 ml |
| 7.5 mM NADH solution | 1 ml |

The above reaction mixture solution (2.9 ml) is taken in a cuvette and subjected to a preliminary heating at 30° C. for about five minutes. Then the reaction is initiated by adding 0.1 ml of an enzyme solution thereto, decrease in absorbance of 340 nm in a spectrophotometer controlled at 30° C. is recorded for 3–4 minutes and, out of its linear portion, the decrease in the absorbance per minute is determined. A blank test is carried out according to the same operations as above except that 0.1M Tris-HCl buffer (pH: 8.3) is added instead of the enzyme solution. The way of expression of an activity of the glutamate dehydrogenase is in such a manner that the amount of the enzyme by which 1 micromole of NADH is oxidized per minute under the above-mentioned conditions is defined as one unit (U).

The present inventors have further carried out extensive studies for preparing a reagent for measuring an amount of ammonia which is with an excellent precision and storage stability in a low cost and found that a glutamate dehydrogenase which is not activated by ADP and is NADH-dependent can be utilized therefor whereby the present invention has been achieved.

The present invention relates to a reagent composition for measuring an amount of ammonia which is characterized in that said composition contains a glutamate dehydrogenase which is not activated by ADP and is NADH-dependent, a-ketoglutaric acid or a salt thereof and NADH.

The present invention further relates to a reagent composition for measuring an amount of urea nitrogen which is characterized in that said composition contains urease, a glutamate dehydrogenase which is not activated by ADP and is NADH-dependent, α-ketoglutaric acid or a salt thereof and NADH.

The present invention still further relates to a reagent composition for measuring an amount of creatinine which is characterized in that said composition contains creatinine deiminase, a glutamate dehydrogenase which is not activated by ADP and is NADH-dependent, α-ketoglutaric acid or a salt thereof and NADH.

With respect to the glutamate dehydrogenase used in the present invention, that prepared from any source may be applied so far as it is not activated by ADP and is NADH-dependent. Preferred glutamate dehydrogenase is that which is derived from the genus Pseudomonas. An example is a glutamate dehydrogenase derived from Pseudomonas sp. 433-3 (FERM-14092) (Japanese Patent Application No. 19448/94).

The physicochemical properties of said enzyme are as follows:

(1) It catalyzes the following reaction.

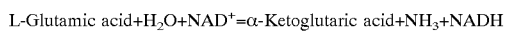

L-Glutamic acid+$H_2O$+$NAD^+$=α-Ketoglutaric acid+$NH_3$+NADH (2) Substrate specificity:

It is specific to L-glutamic acid. It requires $NAD^+$ and NADH as coenzymes and does not act on $NADP^+$ and NADPH.

(3) Optimum pH: 10.5–11.5 (an oxidative deamination)
(4) pH stability: pH 5–10 (at 25° C. for 20 hours)
(5) Optimum temperature: about 60° C. (an oxidative deamination)
(6) Thermal stability: stable up to about 60° C. (at pH 8.3 for ten minutes).
(7) Molecular weight: about 280,000 (by a gel filtration); about 41,000 (by an SDS-PAGE)
(8) It is not activated by ADP.

Said enzyme further exhibits the following properties.

(9) Specific activity: not less than 300 units/mg
(10) Influence of surfactants: not inhibited by Brijs (poloxyethylene long chain alcohol ether)

In the reagent composition of the present invention for the measurement of the amount of ammonia, the preferred amounts of the components are about 0.5–100 U/ml of glutamate dehydrogenase, 1–50 mM of a-ketoglutaric acid and 0.1–1 mM of NADH.

The amount of ammonia in the sample is measured by treating said sample with the above-mentioned reagent composition containing a glutamate dehydrogenase, a-ketoglutaric acid and NADH followed by measuring the absorbance of the consumed NADH.

The amount of the urea nitrogen in the sample is measured in accordance with the present invention by treating said sample with urease, then by treating the ammonia produced thereby with the above-mentioned glutamate dehydrogenase, α-ketoglutaric acid and NADH and by measuring the consumed NADH.

The reagent composition for measuring an urea nitrogen in accordance with the present invention contains urease, glutamate dehydrogenase which is not activated by ADP and is NADH-dependent, α-ketoglutaric acid or a salt thereof and NADH.

With respect to urease used in the present invention, that which is derived from Jack beans is common and is commercially available.

In the reagent composition for measuring the urea nitrogen in accordance with the present invention, the preferred amounts of the components are about 1–30 U/ml of urease, about 0.5–100 U/ml of glutamate dehydrogenase, 1–50 mM of α-ketoglutaric acid and 0.1–1 mM of NADH.

In a method of measuring the amount of creatinine according to the present invention, the sample is treated with a creatinine deiminase and the resulting ammonia is treated with glutamate dehydrogenase, α-ketoglutaric acid and NADH followed by measuring the consumed NADH.

The creatinine deiminase used in the present invention is that produced by a microorganism belonging to the genus Bacillus or to the genus Corynebacterium.

In the reagent for measuring the amount of creatinine according to the present invention, the preferred amounts of the components are about 0.5–10 U/ml of creatinine deiminase, about 0.5–100 U/ml of glutamate dehydrogenase, 1–50 mM of α-ketoglutaric acid and 0.1–1 mM of NADH.

Usually, the reagent composition for measuring the amount of ammonia, urea nitrogen or creatinine is used together with a buffer of pH of about 7–11. Examples of such a buffer are Tris-HCl buffer, triethanolamine-HCl buffer and Good's buffer.

The reagent composition for measuring the amount of urea nitrogen and for ammonia in accordance with the present invention contains a reagent for the elimination of ammonia if necessary. Examples of said reagent are isocitric acid, isocitrate dehydrogenase or ATP, glutamic acid, glutamic acid synthetic enzymes, etc.

Other compounds may be added to the reagent composition of the present invention for conducting the enzymatic reaction smooth. Examples of such compounds are stabilizers, surface-active agents, fillers, etc.

Measurement of NADH is usually carried out by means of an absorptiometry at the wavelength of 340 nm though a subwavelength may be used. Further, double wavelengths including 340 nm may be used for the measurement. Any of an end point assay and a rate assay is carried out for all of the measurement of the amounts of ammonia, urea nitrogen or creatinine.

The method of measuring the amount of ammonia in accordance with the present invention is not limited to the measurement of urea nitrogen and creatinine contained in the sample of the living organisms but also covers the measurement of the amount of ammonia derived from other components.

As a result of the present invention, it is possible to offer a novel glutamate dehydrogenase which is capable of utilizing a less expensive $NAD^+$ (NADH) as a coenzyme, exhibits a high stability and does not require ADP for its activation.

In accordance with the reagent composition of the present invention, there is no need of using ADP which is required for the conventional glutamate dehydrogenase and, in addition, an expensive NADPH is not required too. Moreover, it is possible to offer a reagent composition for the measurement of the amounts of ammonia, urea nitrogen and creatinine with an excellent storage stability for long time. At present time where the use of liquid reagents is spreading, a liquid and stable reagent as such is quite useful.

BRIEF DESCRIPTION OF DRAWINGS

This invention will be further explained by means of the following Examples which refer partly to the accompanying drawings wherein.

EXAMPLE 1

Figure 1:
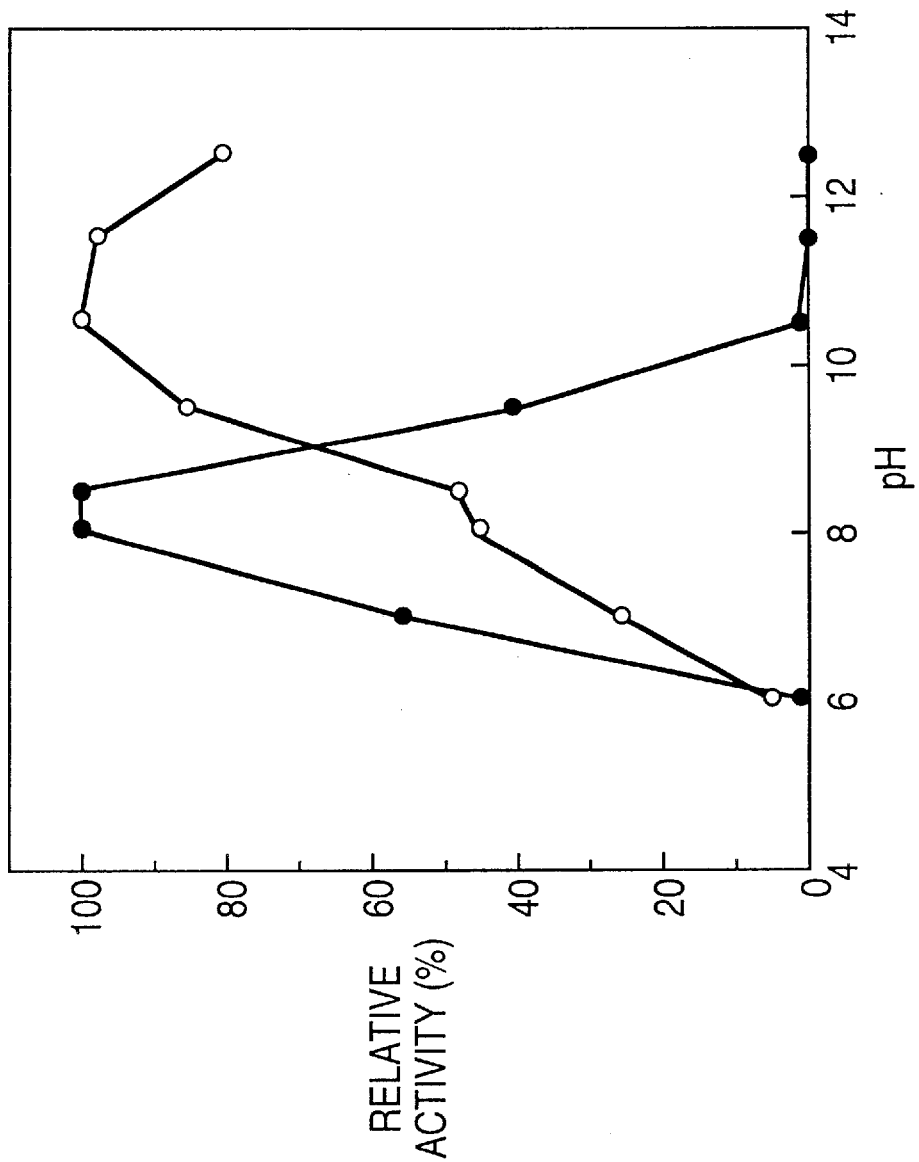
FIG. 1 is a graph showing the relation between the reaction pH and the relative activity of the enzyme.

A culture medium (pH: 7.0) (60 ml) containing 0.6% of sodium glutamate, 1% of polypeptone, 1% of yeast extract and 1% of glycerol was placed in a 500 ml Sakaguchi flask followed by sterilizing (at 121° C. for 15 minutes) and Pseudomonas sp. 433-3 (FERM P-14092) was inoculated and cultured at 30° C. for one day to prepare a seed culture. Then the culture medium (6 liters) was transferred to a 10 liter jar fermentor, autoclaved at 121° C. for 15 minutes, allowed to cool, 60 ml of the seed culture was planted and cultured at 300 rpm and 30° C. with 2 liters/minute of aeration for 24 hours. After completion of the culturing, the cells were collected from the culture and suspended in a 50 mM Tris-HCl buffer (pH: 7.5).

The suspension was treated with a French press and centrifuged to give a supernatant liquid. The resulting crude enzyme solution was fractionated using ammonium sulfate and subjected to a DEAE-Sepharose chromatography, a phenylsepharose chromatography and a gel filtration using Sephadex G-200 to purify to an extent of 300 U/mg of specific activity.

The resulting glutamate dehydrogenase exhibited the following characteristic properties.

(1) It catalyzed the following reaction:

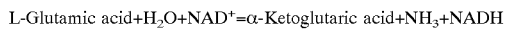

L-Glutamic acid+H$_2$O+NAD$^+$=α-Ketoglutaric acid+NH$_3$+NADH (2) Substrate secificity:

Enzymatic activities when various amino acids were used as substrates were measured. The activities when that to L-glutamic acid was 100 were calculated and given in Table 1.

Measurement of the activity was carried out by the following method.

The following reaction solution was prepared.

| 0.2M Glycine-NaOH buffer (pH: 9.) | 13 ml |
| 0.5M Amino acid | 6 ml |
| 9 mM NAD$^+$ | 2 ml |
| H$_2$O | 8 ml |

The above reaction mixture solution (2.9 ml) was taken in a cuvette and subjected to a preliminary heating at 30° C. for about five minutes. Then the reaction was initiated by adding 0.1 ml of an enzyme solution thereto, a decrease in absorbance of 340 nm in a spectrophotometer controlled at 30° C. was recorded for 3–4 minutes and, out of its linear portion, the decrease in the absorbance per minute was determined. A blank test was carried out according to the same operations as above except that 0.1M Tris-HCl buffer (pH: 9.0) was added instead of the enzyme solution.

TABLE 1

| 1. L-2-Amino-n-butyric acid | 0.106% |
|---|---|
| 2. L-Norleucine | 0.036 |
| 3. L-Glutamic acid | 100 |
| 4. DL-Homocysteine | 0.036 |
| 5. L-Norvaline | 0.21 |
| 6. L-Methionine | 0 |
| 7. L-Leucine | 0 |
| 8. L-Aspartic acid | 0 |
| 9. L-Glutamine | 0 |
| 10. L-α-Alanine | 0 |
| 11. L-Valine | 0 |
| 12. L-Isoleucine | 0 |
| 13. L-Asparagine monohydrate | 0 |

(3) Km value:

The Km value to ammonia was 8.5 mM while the values to NADH, L-glutamic acid and NAD$^+$ were 0.19 mM, 17 mM and 0.10 mM, respectively.

(4) Optimum pH:

The relationship between the enzymatic reaction of the present invention and the relative activity is given in FIG. 1. FIG. 1 is a result of the measurement of the enzymatic activities in 0.1 M Tris-HCl buffer (pH: 6–8) and 0.1M glycine-NaOH buffer (pH: 8.5–12.5) in which o—o and ●—● show an oxidative deamination and a reductive amination, respectively.

The optimum pH for the oxidative deamination was 10.5–11.5 while that for the reductive amination was 8.0–8.5.

Figure 2:
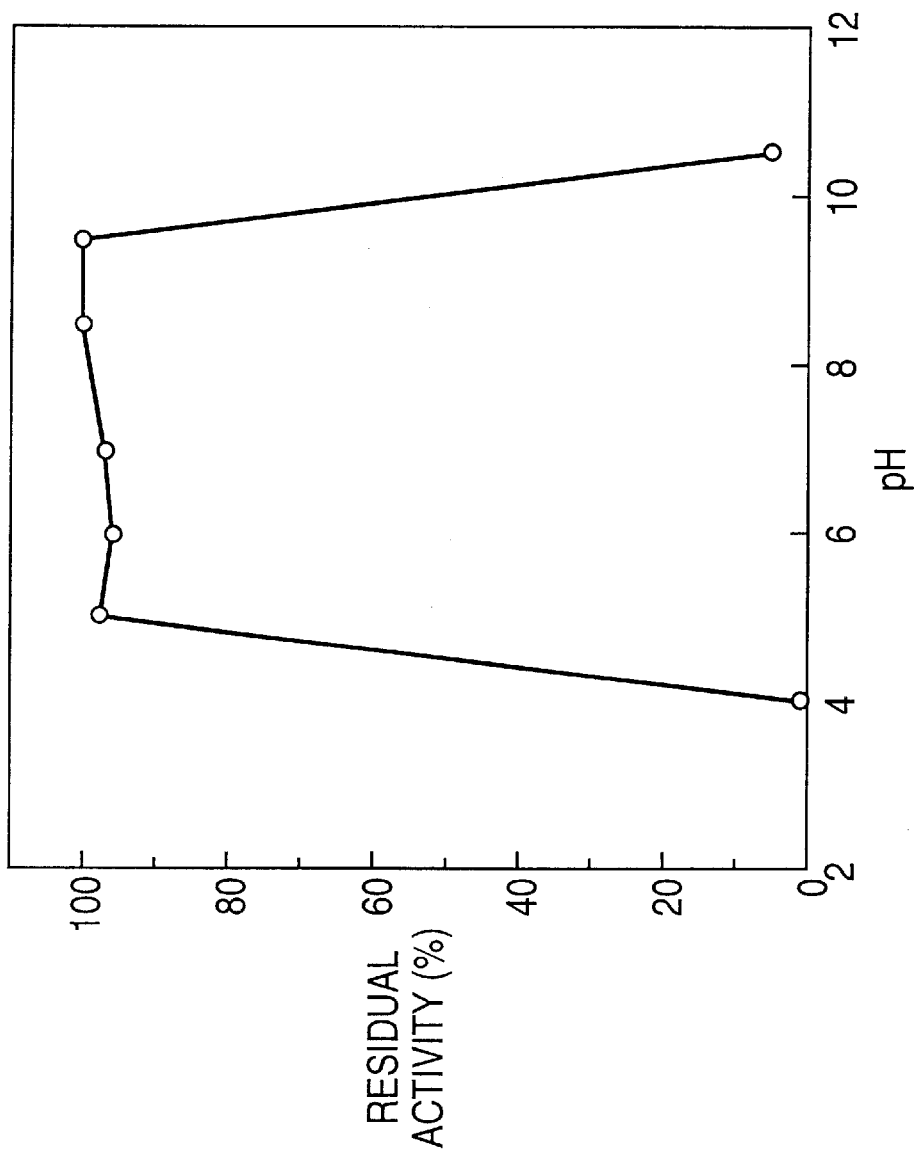
FIG. 2 is a graph showing the pH stability of the enzyme.

(5) pH stability:

The pH stability of the enzyme of the present invention is given in FIG. 2.

FIG. 2 is a result of the measurement of the residual activity after storing at 25° C. for 20 hours in 0.1M acetate buffer (pH: 4–6), 0.1M K-phosphate buffer (pH: 6–8) and 0.1M Tris-HCl buffer (pH: 8–10). The stable pH was at pH 5–10.

Figure 3:
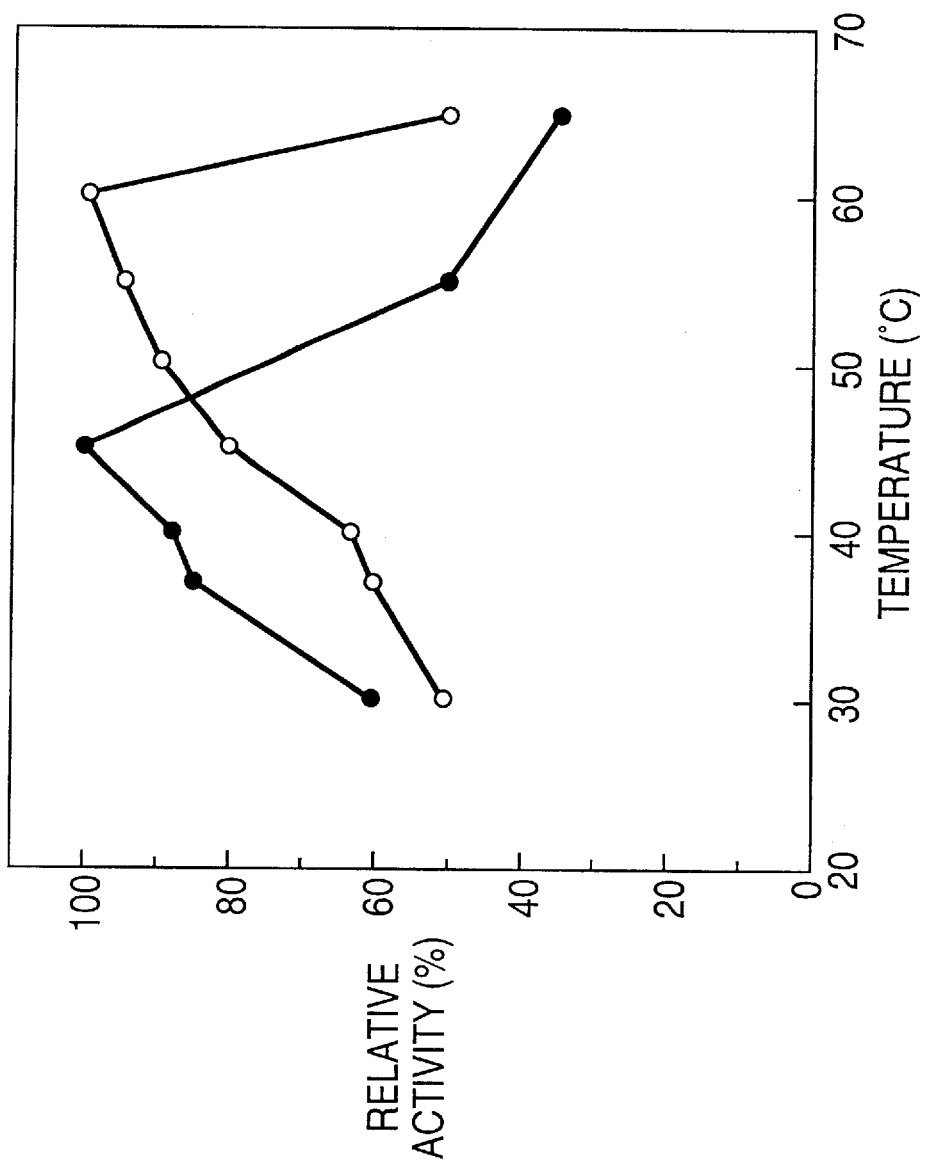
FIG. 3 is a graph showing the relation between the reaction temperature and the relative activity of the enzyme.

(6) Optimum temperature:

FIG. 3 shows the relationship between the reaction temperature and the relative activity of the enzyme of the present invention.

FIG. 3 is a result of the measurement of the enzymatic activities at various temperatures. In the drawing, o—o and ●—● show an oxidative deamination and a reductive amination, respectively.

The optimum temperature for the oxidative deamination was about 60° C. while that for the reductive amination was about 45° C.

Figure 4:
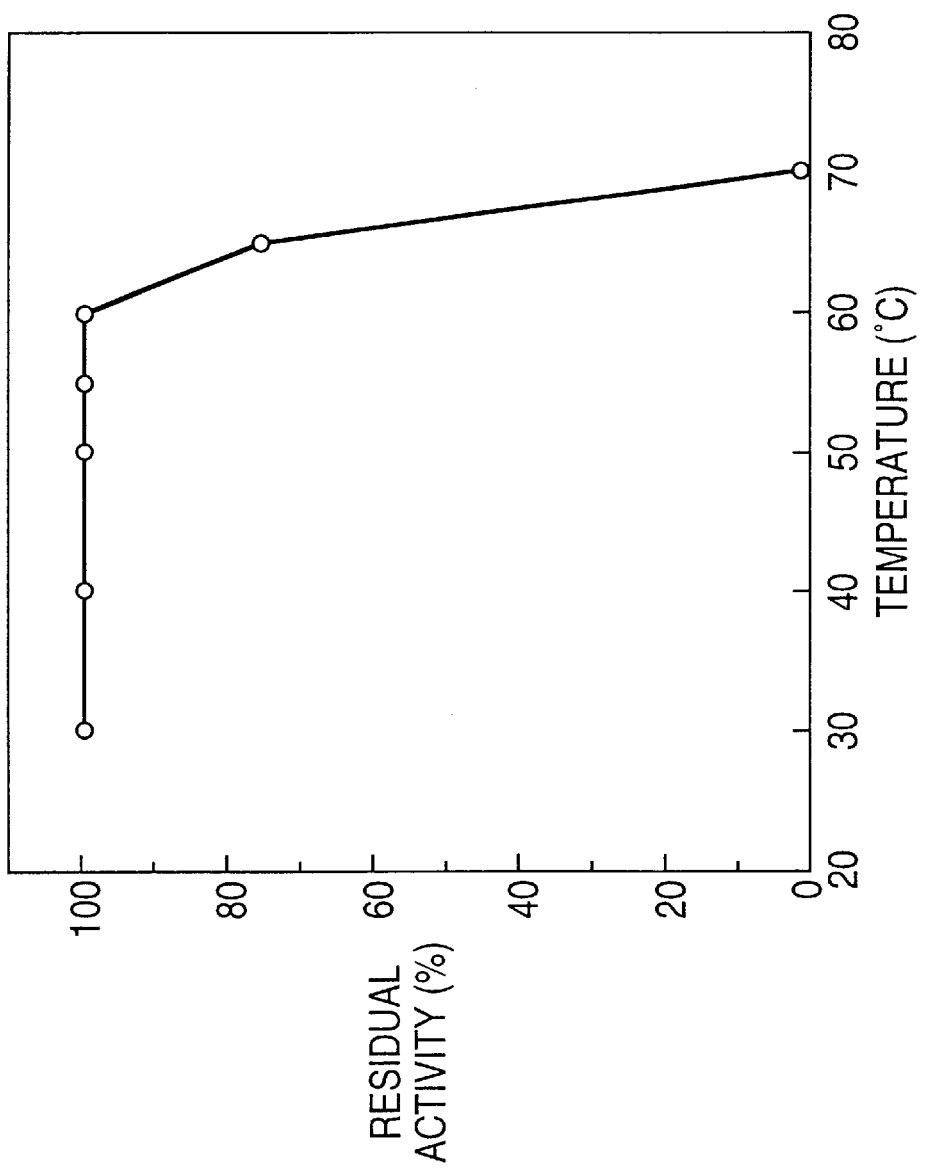
FIG. 4 is a graph showing the thermostability of the enzyme.

(7) Thermal stability:

The thermal stability of the enzyme of the present invention is given in FIG. 4.

FIG. 4 is a result of the measurement of the residual activity after heating in a 0.1M Tris-HCl buffer (pH: 8.3) for ten minutes and the enzyme was stable up to about 60° C.

(8) Molecular weight: About 280,000 (according to a gel filtration method); subunit: About 40,000 (according to an SDS-PAGE)

(9) Isoelectric point: 5.6 (according to an isoelectric electrophoresis)

(10) Activation by ADP:

ADP was added to the reagent for measuring the activity of glutamate dehydrogenase of the present invention (a reductive amination) to make it 2.5 mM and the resulting activity was compared with that where nothing was added.

TABLE 2

|  | This Invention | Bovine Liver GLDH |
|---|---|---|
| without ADP | 100% | 100% |
| with 2.5 mM ADP | 100% | 145% |

(11) Comparison with Known Enzymes:
The properties of the enzyme of the present invention was compared with those of the known NAD$^+$-dependent glutamate dehydrogenase (EC.1.4.1.2).

TABLE 3

| Source | Pseudo-monas sp 433-3 | Peptoco-ccus ae-rogene | Clostri-dium sp. SB4 | Synecho-cystis sp. |
|---|---|---|---|---|
| Reference | This In-ven-tion | Can.J. Micro-biol.18, 881(1972) | The Enz-ymes,3rd Ed. 11, 293(1975) | FEBS Lett. 285, 35(1991) |
| Molecular weight (Gel Filtration) | 280000 | 266000 | 268000–282000 | 295000 |
| (SDS-AGE) | 41000 | 49000 | — | 48500 |
| Optimum Temperature | 60° C. | 50–55° C. | — | — |
| Optimum pH | | | | |
| (Oxid.Deamination) | 10.5–11.5 | 8.8–8.9 | 9.4 | 9.5–10.0 |
| (Red.Amination) | 8.0–8.5 | | 7.8 | 8.5–9.0 |
| Km Value to NH$_3$ (mM) | 8.5 | 18.4 | 0.32 | 4.5 |

EXAMPLE 2

The reagent solution having the following composition was prepared.

| Glutamate dehydrogenase (Pseudomonas sp.433-3) | 0.3 U/ml |
|---|---|
| Urease (Product of Toyo Boseki K.K.) | 10 U/ml |
| α-Ketoglutaric acid | 10 mmol/ml |
| NADH | 0.3 mmol/ml |
| TritonX-100 | 0.1% |
| Tris-HCl buffer | 50 mmol/l (pH: 8.5) |

Figure 5:
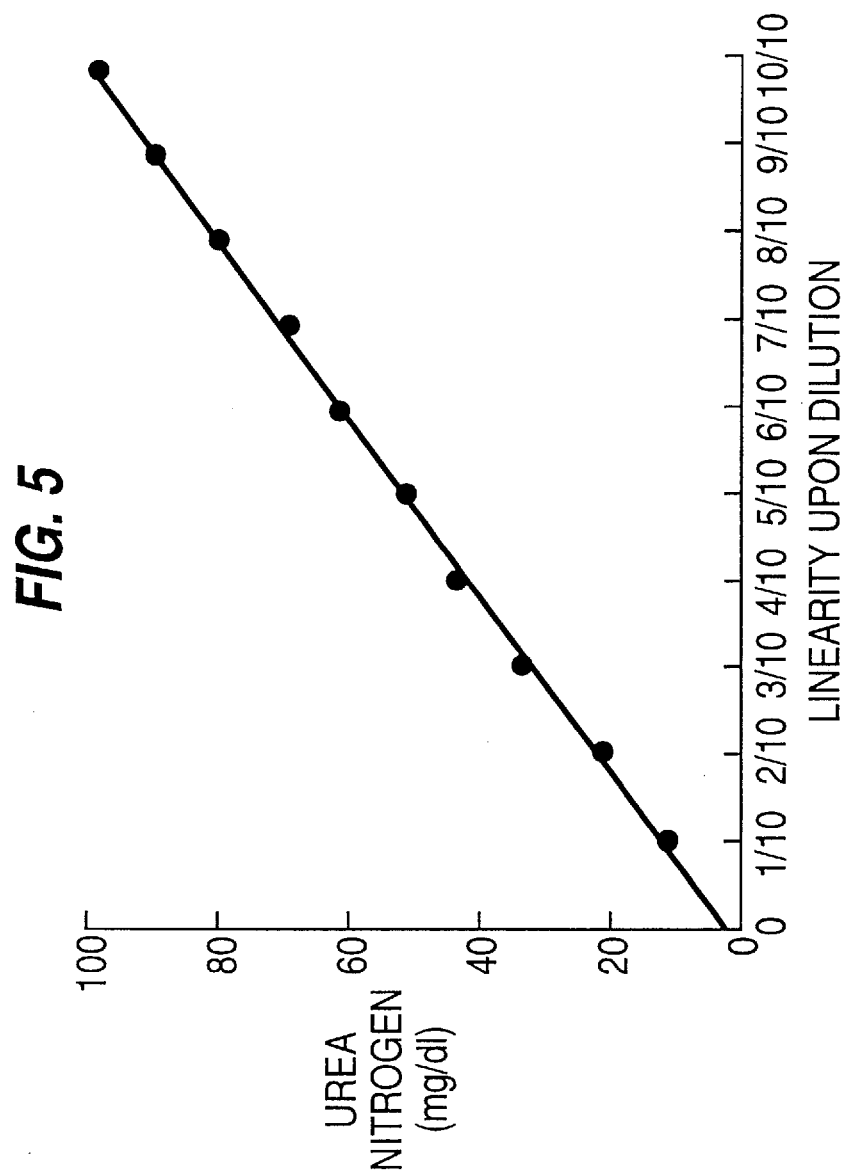
FIG. 5 is a graph showing a linear relationship with a dilution of the urea nitrogen when the reagent composition for measuring the amount of the urea nitrogen according to the present invention is used.

The above-given reagent solution (3 ml) was preliminarily warmed at 37° C. for five minutes and each 0.05 ml of samples in which 100 gm/gl of urea nitrogen was diluted in ten gradients was added and was made to react at 37° C. for three minutes to measure a decrease in the absorbancy at 340 nm per minute. The result is given in FIG. 5 and the linearity was noted up to 100 mg/dl of an urea nitrogen.

EXAMPLE 3

Figure 6:
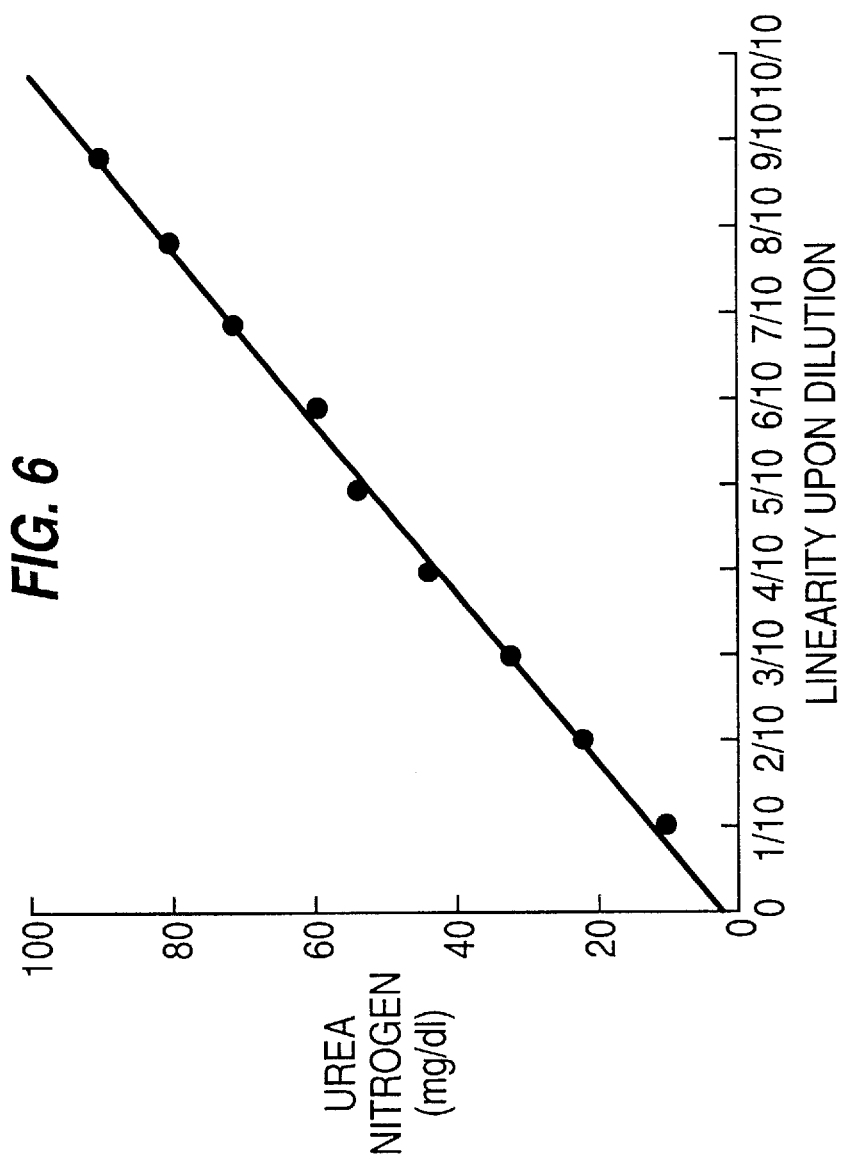
FIG. 6 is a graph shownig a linear relationship with a dilution of the urea nitrogen when the reagent composition for measuring the amount of the urea nitrogen according to the present invention is used after storing at 25° C. for one week.

The reagent solution of the composition of Example 1 was stored at 25° C. for one week and a measurement was conducted for the samples diluted in ten gradients. The result is given in FIG. 6 and, even after stored for one week at 25° C., the linearity was found to be maintained up to 100 mg/dl of urea nitrogen.

EXAMPLE 4

A reagent solution having the following composition was prepared.

| Glutamate dehydrogenase (Pseudomonas sp. 433-3) | 20 U/ml |
|---|---|
| Creatinine deiminase (Product of Toyo Boseki KK) | 10 U/ml |
| α-Ketoglutaric acid | 12 mmole/l |
| NADH | 0.4 mmol/l |
| Tris-HCl buffer | 50 mmol/l, pH: 8.3 |

Figure 7:
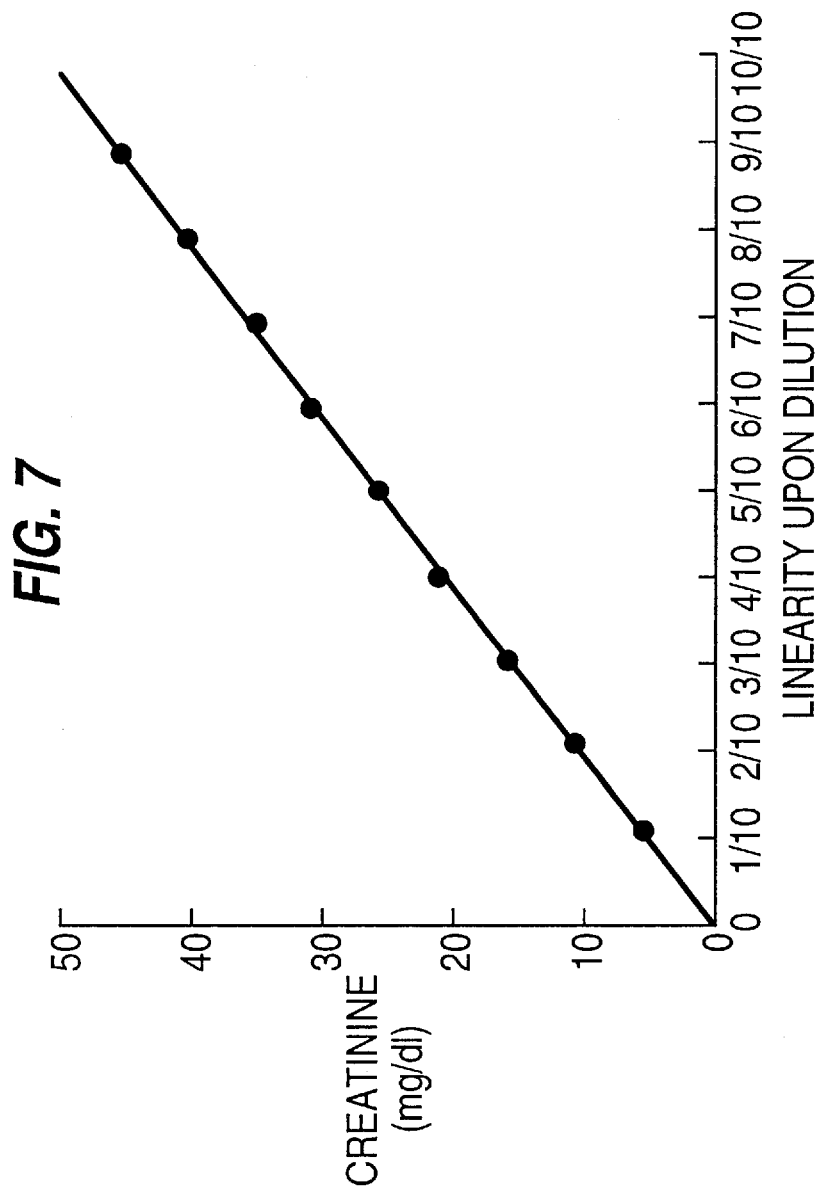
FIG. 7 is a graph showing a linear relationship with a dilution of creatinine when the reagent composition for measuring the amount of creatinine according to the present invention is used.

The above reagent solution (3 ml) was preliminarily warmed at 30° C. for five minutes, each 0.1 ml of samples in which 50 mg/dl of creatine was diluted in ten gradients was added, the reaction was carried ut at 30° C. and, out of the absorbance at 340 nm after three minutes, a decrease in the absorbance at 340 nm after one minute was calculatd. The result is given in FIG. 7 and there was a proportional relationship up to 50 mg/dl of creatinine.

Comparative Example 1

The reagent solution having the following composition was prepared.

| Glutamate dehydrogenase (derived from bovine liver) | 0.3 U/ml |
|---|---|
| Urease (Product to Toyo Boseki K.K.) | 10 U/l |
| α-Ketoglutaric acid | 10 mmol/l |
| NADH | 0.3 mmol/l |
| Triton X-100 | 0.1% |
| Tris-HCl buffer | 50 ml/l; pH: 8.5 |

Figure 8:
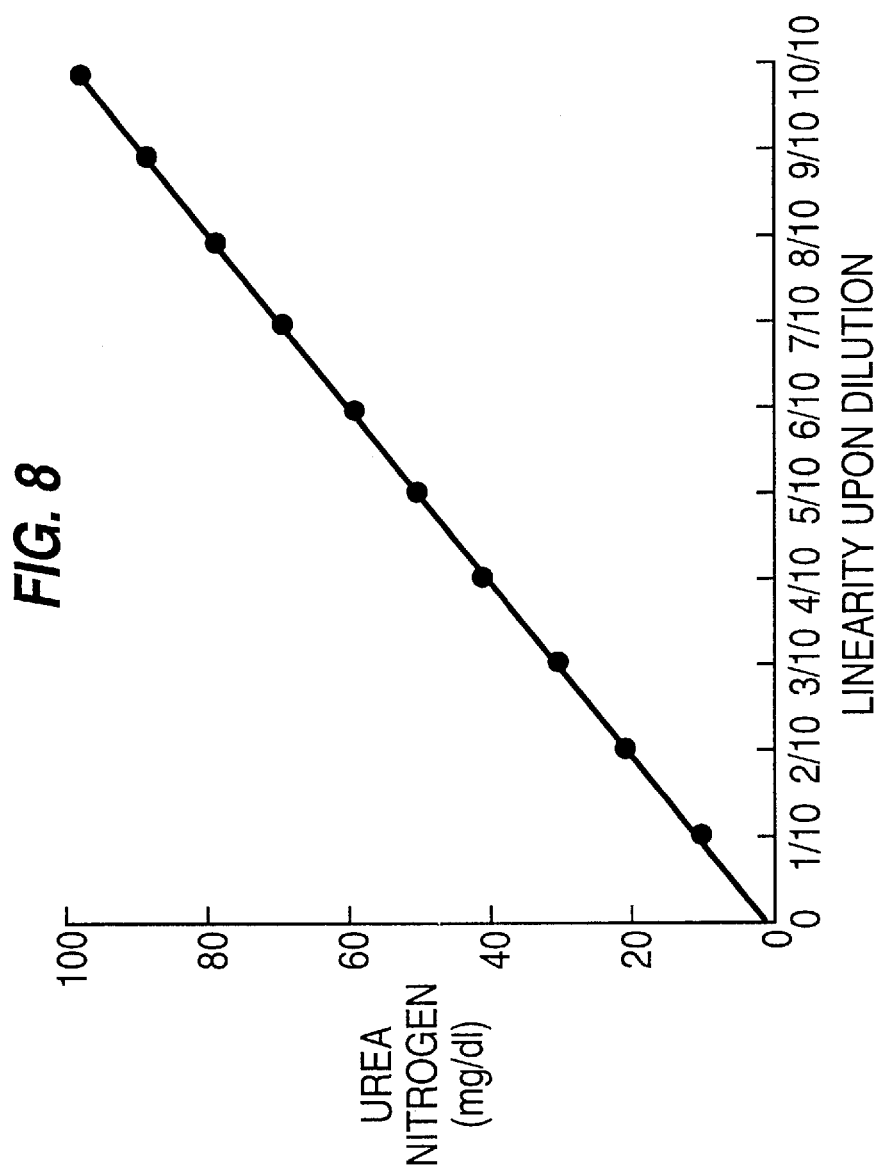
FIG. 8 is a graph showing a linear relationship with a dilution of the urea nitrogen when the reagent composition for measuring the amount of the urea nitrogen according Comparative Example 1 is used.

The above reagent solution (3 ml) was preliminarily warmed at 37° C. for five minutes, each 0.05 ml of the samples in which 100 mg/dl of Area nitrogen was diluted in ten gradients was added, the reaction was carried out at 37° C. for three minutes and a decrease in an absorbance at 340 nm per minute was measured. The result is given in FIG. 8 and there was a linearity up to the 100 mg/dl of urea nitrogen.

Figure 9:
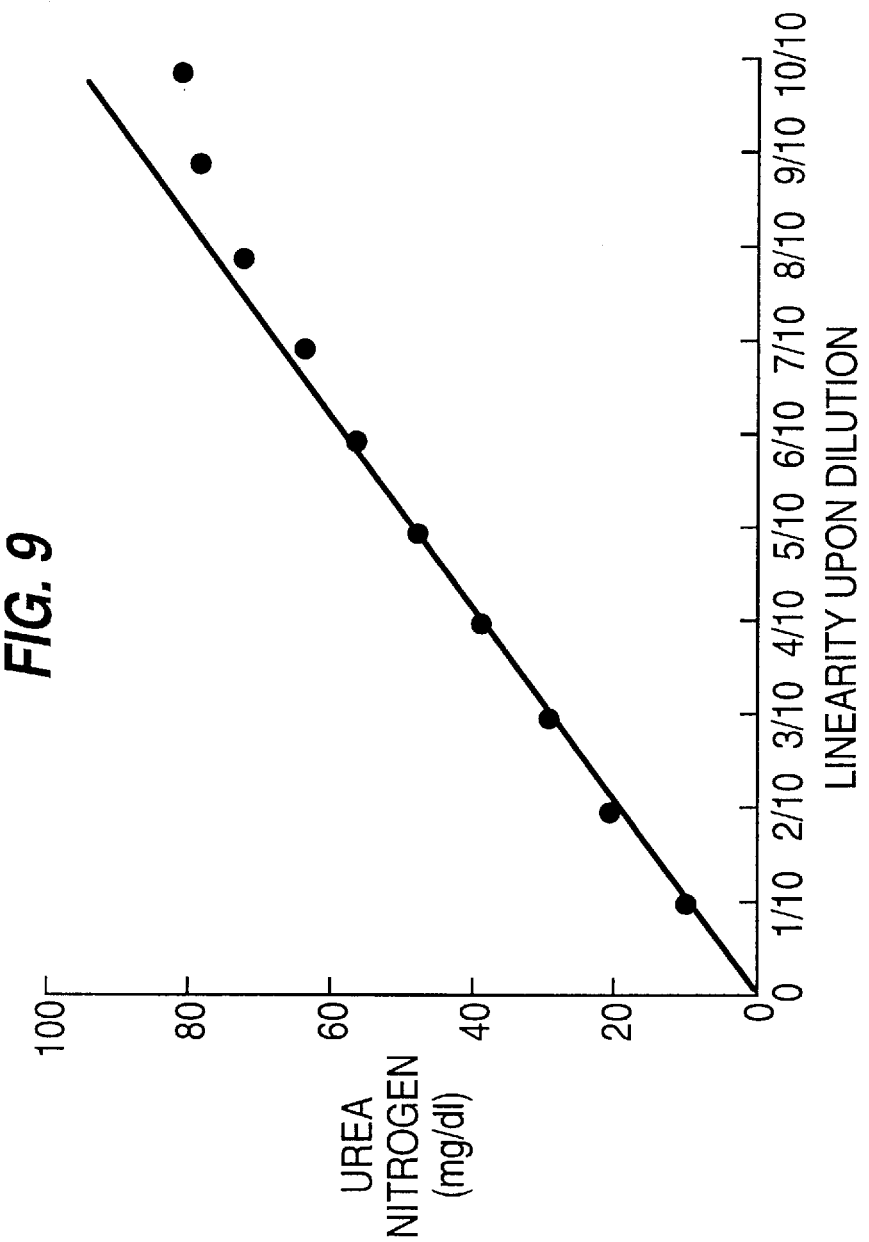
FIG. 9 is a graph showing a linear relationship with a dilution of the urea nitrogen when the reagent composition for measuring the amount of the urea nitrogen according to Comparative Example 1 is used after storing at 25° C. for one week.

The reagent solution of the above composition was stored at 25° C. for one week and the measurements were conducted for the samples diluted in ten gradients. The result is given in FIG. 9 and the linearity after stored at 25° C. for one week was available up to 60 mg/dl of urea nitrogen and, since the enzyme derived from bovine liver was unstable without ADP, it did not exhibit a quantitative proportional relationship beyond that concentration.

EXAMPLE 5

The reagent solution having the following composition was prepared.

| α-Ketoglutaric acid | 7.6 mmol/l |
|---|---|
| NADH | 0.25 mmol/l |
| EDTA | 0.85 mmol/l |
| Tris-HCl buffer | 85 mmol/g; pH: 8.3 |
| NH$_4$Cl | 0.22M |
| Brij 35 or 58 | 0.05% or 0.1% |

Figure 10:
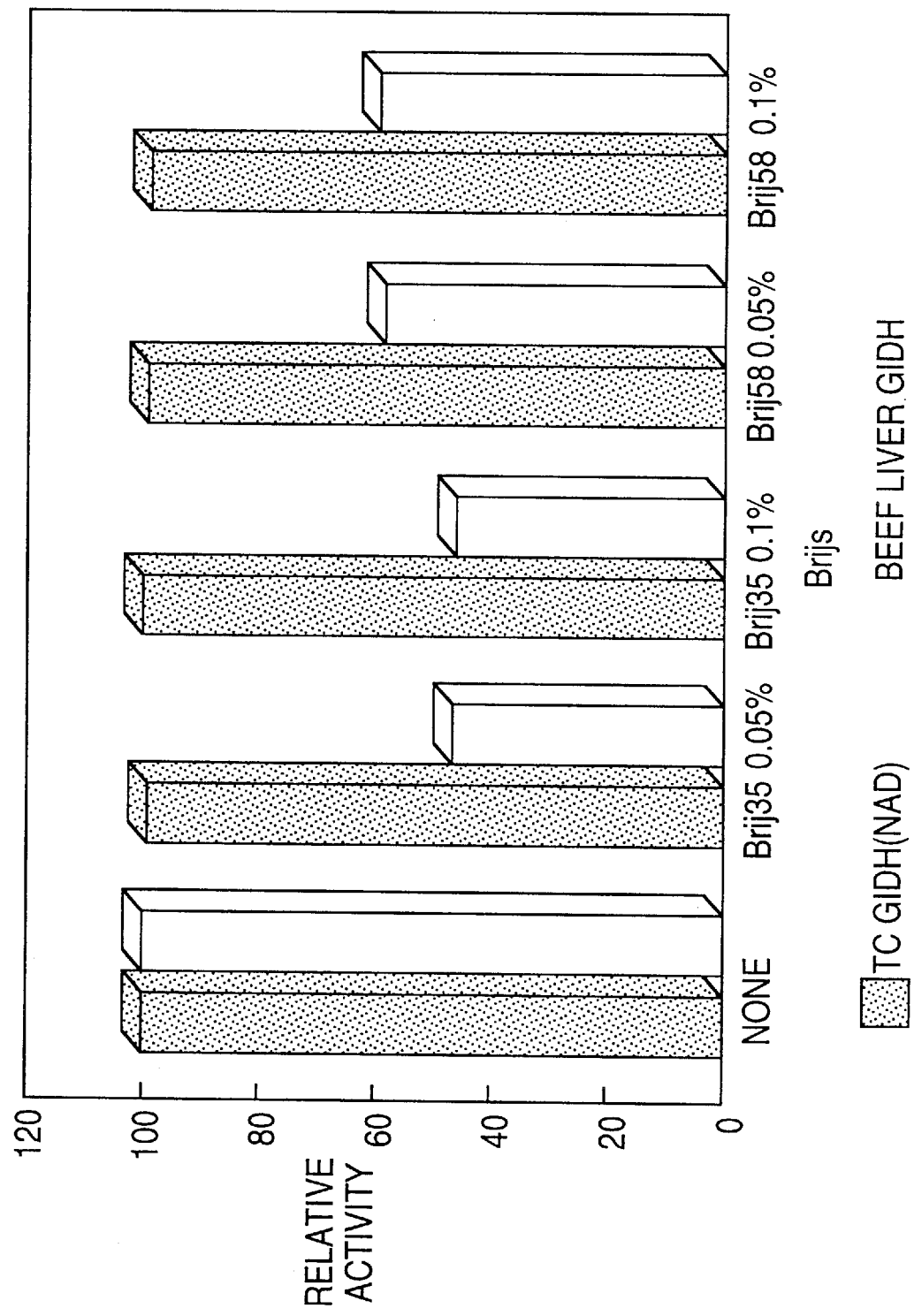
FIG. 10 is a graph showing an effect of a surface-active agent Brij on the enzyme of the present invention.

The above reagent solution (2.9 ml) was preliminarily warmed at 30° C. for five minutes, 0.05 ml of the glutamate dehydrogenase (0.6 U/ml) of the present invention was added thereto, the reaction was carried out at 30° C. for three minutes and a decrease in the absorbance at 340 nm per minute was measured. The result is given in FIG. 10 and neither Brij 35 nor 58 showed an affection.

For comparison, 2.9 ml of the above reagent solution (except that ADP was added to make 10 mmol/l) was preliminarily warmed at 30° C. for five minutes, 0.05 ml of a glutamate dehydrogenase (0.6 U/ml) derived from bovine liver was added thereto, the reaction was carried out at 30° C. for three minutes and a change in the absorption at 340 nm per minute was measured. The result is given in FIG. 10 and the activity was inhibited to an extent of about 50% and 40% by Brij 35 and Brij 58, respectively.

What we claim is:

1. An isolated, purified, water soluble glutamate dehydrogenase produced by Pseudomonas sp. 433-3 having the following physicochemical properties;

(a) it catalyzes the following reaction

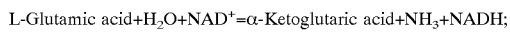
   L-Glutamic acid+$H_2O$+$NAD^+$=α-Ketoglutaric acid+$NH_3$+NADH;

(b) it has a substrate specificity to L-glutamic acid; it requires $NADP^+$ and NADH as coenzymes and does not act on $NADP^+$ and NADPH;
   (c) it is thermally stable up to about 60° C. at a pH of 8.3 for ten minutes; and
   (d) it is not activated by ADP.

2. The isolated purified, water soluble glutamate dehydrogenase according to claim 1, having the following additional physicochemical properties:

(e) a specific activity of not less than 300 units/mg; and
   (f) it is not inhibited by polyoxyethylene long chain alcohol ether.

3. The isolated purified, water soluble glutamate dehydrogenase according to claim 1, having the following additional physicochemical properties:

(g) an optimum pH for oxidative deamination of 10.5–11.5;
   (h) a pH stability of 5–10 at 25° C. for 20 hours;
   (i) an optimum temperature for oxidative deamination of about 60° C.; and
   (j) a molecular weight of about 280,000 measured by gel filtration, and of about 41,000 when measured by SDS-PAGE.

4. The isolated purified, water soluble glutamate dehydrogenase according to claim 3, having the following additional physicochemical properties:

(e) a specific activity of not less than 300 units/mg; and
   (f) it is not inhibited by polyoxyethylene long chain alcohol ether.

5. The isolated purified, water soluble glutamate dehydrogenase according to claim 1, wherein the purification is accomplished by fractionation using ammonium sulfate, DEAE-Sepharose chromatography, phenylsepharose chromatography, and gel filtration.

* * * * *